United States Patent [19]

Broderick

[11] Patent Number: 5,171,285
[45] Date of Patent: Dec. 15, 1992

[54] ACETABULAR CUP WITH SHIFTABLE ELEVATED RIM LINER

[75] Inventor: Melissa A. Broderick, Warsaw, Ind.
[73] Assignee: Zimmer, Inc., Warsaw, Ind.
[21] Appl. No.: 836,439
[22] Filed: Feb. 18, 1992
[51] Int. Cl.⁵ .............................................. A61F 2/34
[52] U.S. Cl. ..................................................... 623/22
[58] Field of Search ........................ 623/16, 18, 19, 20, 623/22, 23

[56] References Cited

U.S. PATENT DOCUMENTS

| | | | |
|---|---|---|---|
| 4,623,351 | 11/1986 | Church | 623/22 |
| 4,650,491 | 3/1987 | Parchinski | 623/22 |
| 4,678,472 | 7/1987 | Noiles | 623/22 |
| 4,695,282 | 9/1987 | Forte et al. | 623/22 |
| 4,950,299 | 8/1990 | Noiles | 623/22 |
| 4,978,356 | 12/1990 | Noiles | 623/22 |
| 5,002,577 | 3/1991 | Bolesky et al. | 623/22 |
| 5,049,158 | 9/1991 | Engelhardt et al. | 623/22 |
| 5,092,897 | 3/1992 | Forte | 623/22 |

Primary Examiner—David Isabella
Attorney, Agent, or Firm—Todd A. Dawson

[57] ABSTRACT

The acetabular cup assembly of this invention includes a bearing component having an elevated rim and a metal cup. A groove is formed about the component for engagement with a locking ring carried by the metal cup. The bearing component may be inserted into the cup and tilted or tipped so that the elevated rim is pressed downwardly against the rim of the metal cup. In this position, the elevated portion of the rim is out of the way of the surgeon permitting the head to be more easily inserted into the bearing component. Once the head is seated the surgeon presses against the raised lip of the bearing component to shift the bearing component such that the elevated lip is properly positioned. A snap ring locks into a groove of the bearing component when positioned for use.

Accordingly, it is an obejct of the invention to provide a novel acetabular hip cup assembly.

Another object of the invention is to provide an acetabular hip cup assembly wherein the bearing component may be shifted to place the elevated lip in a generally parallel relationship relative to the rim of the metal cup.

2 Claims, 1 Drawing Sheet

ACETABULAR CUP WITH SHIFTABLE ELEVATED RIM LINER

FIELD OF THE INVENTION

This invention relates to an acetabular cup having an elevated rim liner which is shiftable to facilitate reduction of the prosthetic hip joint.

BACKGROUND OF THE INVENTION

Prosthetic acetabular hip cup assemblies are well known in the field of orthopaedic surgery. Acetabular hip cup assemblies having elevated rims are also well known in the art. Examples of prior art acetabular hip cup assemblies with elevated rims and attached by snap rings are illustrated in the following U.S. patents:

Engelhardt, et al. U.S. Pat. No. 5,049,158 discloses an acetabular cup assembly having a bearing component and a metal acetabular cup component held in a locked relationship by a wire formed about the periphery of the bearing component. The bearing component includes an elevated rim which contacts the rim of the metal cup.

Forte, et al. U.S. Pat. No. 4,695,282 disclosed an acetabular cup assembly having a bearing component and a metal cup. The bearing component may be temporarily positioned within the cup prior to locking engagement to permit the surgeon to check the orientation of the cup and bearing component. To lock the two components together, the bearing component is pressed further into the cup wherein a locking ring engages the cup. When locked, the elevated rim of the bearing component contacts the rim of the cup.

Parchinski U.S. Pat. No. 4,650,491 discloses an acetabular cup assembly wherein the bearing component includes a plurality of rings which engage a groove in the metal cup to lock the two components together. In use the elevated rim of the bearing component contacts the rim of the metal cup.

During a procedure to implant the prosthetic acetabulum and hip stem, to reduce the joint the surgeon must negotiate around the elevated rim to seat the femoral head within the bearing component.

SUMMARY OF THE INVENTION

The acetabular cup assembly of this invention includes a bearing component having an elevated rim and a metal cup. A groove is formed about the component for engagement with a locking ring carried by the metal cup. The bearing component may be inserted into the cup and tilted or tipped so that the elevated rim is pressed downwardly against the rim of the metal cup. In this position, the elevated portion of the rim is out of the way of the surgeon permitting the head to be more easily inserted into the bearing component. Once the head is seated the surgeon presses against the raised lip of the bearing component to shift the bearing component such that the elevated lip is properly positioned. A snap ring locks into a groove of the bearing component when positioned for use.

Accordingly, it is an object of the invention to provide a novel acetabular hip cup assembly.

Another object of the invention is to provide an acetabular hip cup assembly wherein the bearing component may be shifted to place the elevated lip in a generally parallel relationship relative to the rim of the metal cup.

Another object of the invention is to provide a novel acetabular hip cup assembly having a shiftable bearing component.

Still other objects of the invention will become apparent upon a reading of the following description taken with the accompanying drawings.

DESCRIPTION OF THE PREFERRED EMBODIMENT

The preferred embodiment herein described is not intended to be exhaustive or to limit the invention to the precise form disclosed. Rather, it is chosen and described to best explain the invention so that others skilled in the art might utilize its teachings.

Figure 2:
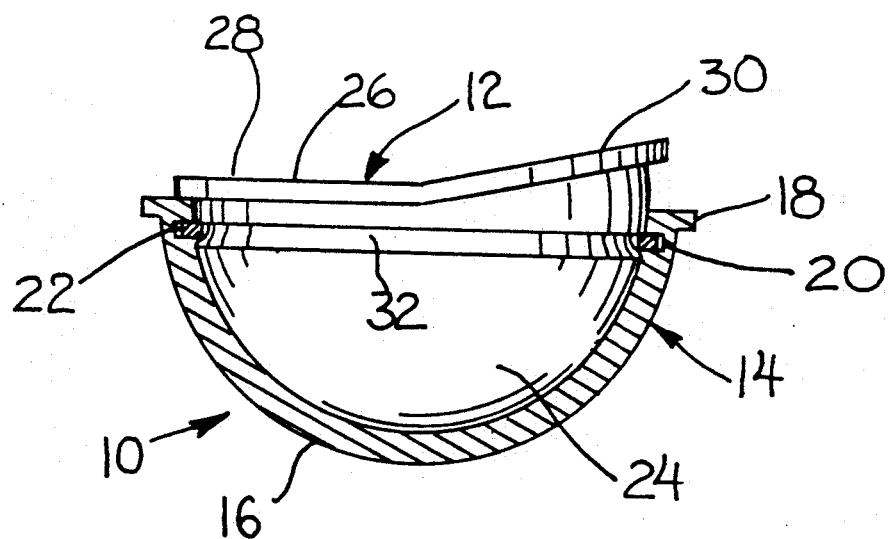
FIG. 2 is the view of FIG. 1 with the bearing component positioned for use.

The acetabular hip cup assembly 10 of the invention is illustrated in the figures as including a bearing component 12 and a metal cup component 14. The cup component 14 includes a hemispherical body 16 and a peripheral lip 18. An internal groove 20 is formed within the cup adjacent the lip 18. A snap ring 22 is carried within groove 20. Bearing component 12 includes a generally hemispherical body 24 and a lip 26. As illustrated in the figures, lip 26 includes a portion 28 which is generally parallel to lip 18 when the bearing component is in the locked position of FIG. 2 and an elevated portion 30 which is spaced from lip 18 when the bearing component is in the locked position of FIG. 2. A groove 32 is formed about body 24 adjacent lip 26.

Figure 1:
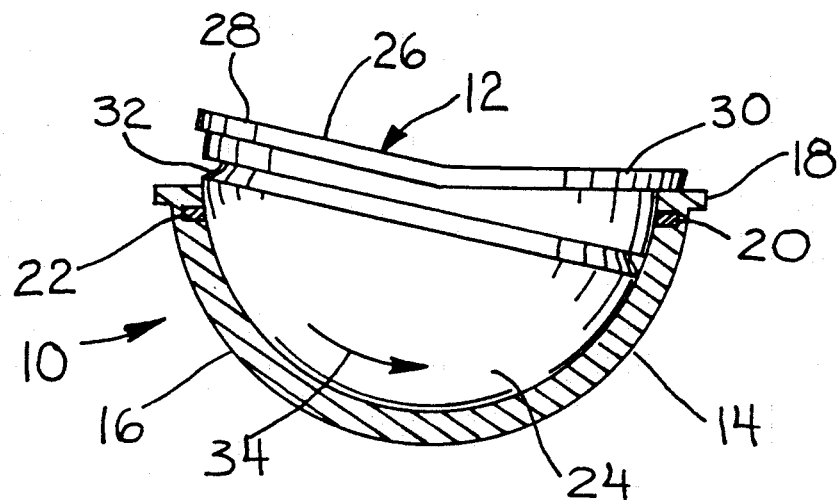
FIG. 1 is a side elevational view of the acetabular cup assembly with the bearing component positioned to permit the femoral head to be inserted into the bearing component. Portions are sectioned for illustrative purposes.

In use, the metal cup is attached to the prepared acetabulum by appropriate surgical techniques well known in the art. The bearing component 12 is placed within the cup 14 as illustrated in FIG. 1 such that elevated lip portion 30 abuts lip 18 of the cup. As illustrated in FIG. 1, in this position groove 32 is not aligned with ring 22. In this position, a femoral head of a prosthetic hip stem (not shown) may be seated in the bearing component by passing over the elevated lip portion 30. Once the femoral head is properly positioned within the bearing component, the surgeon pushes against lip portion 28 to rotate the bearing component in the direction of arrow 34 until lip 28 contacts lip 18 of the cup. Snap ring 22 slides into groove 32 to lock the bearing component to the metal cup component. In the locked position of FIG. 2, elevated lip portion 30 is held at an angle relative to lip 18 and is generally spaced therefrom.

It should be understood that once the two components are locked together by snap ring 22, the intended use requires the two components to remain fixed together.

It should also be understood that the invention is not to be limited to the precise form disclosed above, but may be modified within the scope of the appended claims.

I claim:

1. An acetabular cup assembly comprising a cup component, a bearing component and means for retaining said bearing component to said cup component, said cup component including a shell terminating in an annular flange, said bearing component including a body with a peripheral lip, said lip having first and second portions, each portion defining respective planes which intersect one another at an angle whereby said bearing component is shiftable between an unlocked position and locked position such that with said bearing in said unlocked position, said first portion is in horizontal contact with said flange and said second portion is spaced from said flange, and in said locked position said second portion is in horizontal contact with said flange and said first portion is elevated from said flange with said retaining means being in locking engagement with each of said bearing component and said cup to lock said bearing component against movement relative to said cup.

2. The acetabular component of claim 1 wherein said retaining means includes a snap ring shiftably carried within an annular groove in said cup component, said bearing component body including an annular groove for accommodating a portion of said snap ring in an interference fit when said bearing component is positioned in said locked position.

* * * * *